United States Patent [19]

Kuramochi

[11] Patent Number: 4,908,438

[45] Date of Patent: Mar. 13, 1990

[54] DAUNORUBICIN, DOXORUBICIN AND PHARMACEUTICALLY ACCEPTABLE SALTS THEREFORE AS ANTI-RETROVIRAL AGENTS

[75] Inventor: Tsuneo Kuramochi, Tokyo, Japan

[73] Assignee: Meiji Seika Kaisha, Ltd., Tokyo, Japan

[21] Appl. No.: 200,609

[22] Filed: May 31, 1988

[30] Foreign Application Priority Data

Jun. 10, 1987 [JP] Japan .................................. 62-145538

[51] Int. Cl.$^4$ ............................................. A61K 31/71
[52] U.S. Cl. ..................................................... 536/6.4
[58] Field of Search ............................ 536/6.4; 514/34

[56] References Cited

U.S. PATENT DOCUMENTS

| | | | |
|---|---|---|---|
| 4,098,884 | 7/1978 | Arcamone | 536/6.4 |
| 4,131,649 | 12/1978 | Penco | 536/6.4 |
| 4,138,480 | 2/1979 | Gosalvez | 536/6.4 |
| 4,211,864 | 7/1980 | Vicario | 536/6.4 |
| 4,218,440 | 8/1980 | Penco | 536/6.4 |

Primary Examiner—Ronald W. Griffin
Assistant Examiner—Pamela S. Webber
Attorney, Agent, or Firm—Jordan and Hamburg

[57] ABSTRACT

Anti-retroviral agents comprising, as active ingredient, an antibiotic of anthracycline family (e.g., daunorubicin and doxorubicin) have higher effect with less toxicity, compared with conventional antiretroviral substances, such as azidothymidine and bleomycin.

3 Claims, No Drawings

DAUNORUBICIN, DOXORUBICIN AND PHARMACEUTICALLY ACCEPTABLE SALTS THEREFORE AS ANTI-RETROVIRAL AGENTS

BACKGROUND OF THE INVENTION

1. Field of the Invention

This invention relates to drugs for the treatment of acquired immunodeficiency syndrome (AIDS) and adult T-cell leukemia (ATL).

2. Description of the Prior Art

As anti-retroviral agents are known antimonious tungstate, suramin, ribavirin, isoprinosine and azidothymidine. But any of these is unsatisfactory in terms of antiviral activity and toxicity, and there is a great demand for better anti-retroviral agents.

SUMMARY OF THE INVENTION

The object of this invention is to provide new anti-retroviral agents free of the above-mentioned problems associated with the conventional agents.

We discovered that antibiotics of anthracycline family, such as daunorubicin (daunomycin) and doxorubicin (adriamycin), which are known to show anti-tumor activity, also have anti-retroviral activity. This invention was accomplished on the basis of these findings.

Thus, this invention relates to anti-retroviral agents comprising an antibiotic of anthracycline family as active ingredient.

The anthracycline antibiotics used in this invention include daunorubicin and doxorubicin. As stated above, these compounds are commercially available as anti-tumor agents, with the acute toxicity (LD50 value) being 14.3 to 19.0 mg/Kg for daunorubicin (intraperitoneal injection on rats) and 21.1 mg/Kg for doxorubicin (intravenous injection on mice).

The anti-retroviral agents of this invention comprising an antibiotic of anthracycline family may be used as parenteral injections (e.g., for intramuscular and intravenous injection and for intravenous instillation), oral preparations (e.g., capsules, tablets, granules, powders and solutions), or external preparations (e.g., ointments, suppositories and tinctures). The suitable dose of the active ingredient (antibiotic of anthracycline family) may vary with the activity, toxicity, administration method and dosage form of the compound used, the condition, sex and age of patient, and other factors, but is generally in the range from 4 to 800 mg per day for adults.

The agents of this invention are effective not only for patients infected with retroviruses, but also for retrovirus carriers (those who have been infected but show no symptom yet).

The anti-retroviral agents of this invention can be prepared by usual methods using additives commonly employed in pharmaceutical manufacturing. Parenteral injections may be manufactured by charging ampules with a solution containing the active ingredient, or the solution is freeze-dried in a vial, and the frozen product is dissolved before use. Oral preparations can be manufactured by mixing the active ingredient with an excipient, stabilizer, preservative, dispersant, luburicant and other necessary components and, treating the mixture into a desired dosage form. External preparations can be manufactured by combining the active ingredient with a base material, stabilizer, preservative, surfactant and others.

Described below is the anti-retroviral action of the antibiotics of anthracycline family.

Among the viruses isolated from patients infected by retroviruses are HIV (human immunodeficiency virus) and HTLV-I (human T-lymphotrophic virus-I), which are both retroviruses. On the other hand, FeLV (feline leukemia virus), which is known to cause AIDS and T-cell leukemia of cats, is also a kind of retrovirus having properties very similar to those of HTLV-I and very closely related thereto in viral taxonomy. Hence, we conducted a screening test for anti-retroviral agents using FeLV-producing cells and found that daunorubicin and doxorubicin have outstandingly high activity against retroviruses.

TEST PROCEDURE

FL74 cells (FeLV-producing cells) were dispersed in a liquid medium containing 10% fetal bovine serum to a concentration of $1 \times 10^6$ cell/ml, a drug being tested was added to the dispersion to a predetermined concentration, and the reaction was allowed to proceed at 37° C. for 1 to 6 hours. The reaction mixture was then diluted to a concentration of $1 \times 10^5$ cell/ml, the diluted samples were transferred to a microplate and incubated at 37° C., and production of the virus was checked by the enzyme-linked immunosorbent assay (ELISA) after 24, 48 and 72 hours.

RESULT

The results are shown in Table 1. As can be seen from the table, daunorubicin and doxorubicin showed higher anti-retroviral activity compared with azidothymidine and bleomycin.

TABLE 1

| Drug | Concentration (μg/ml) | Treating Time (hrs) | Production of Virus |
|---|---|---|---|
| Daunorubicin | 1 | 1 | ± |
| | 5 | 1 | − |
| | 0.05 | 6 | − |
| | 0.1 | 5 | − |
| | 0.2 | 5 | − |
| | 0.5 | 5 | − |
| Doxorubicin | 0.1 | 5 | + |
| | 0.1 | 6 | − |
| Azidothymidine | 10 | 1 | + |
| Bleomycin | 50 | 6 | + |

The above result clearly indicates that the anti-retroviral agents of this invention have a higher effect with less toxicity, compared with conventional drugs.

Described below are typical examples for pharmaceutical preparations of the agents of this invention.

EXAMPLE 1 (PREPARATIONS FOR INTRAVENOUS INJECTION)

Daunorubicin hydrochloride was dispensed in vials with 20 mg contained in each (the content is dissolved before use by addition of physiological saline).

EXAMPLE 2 (CAPSULES)

| Daunorubicin hydrochloride | 20 parts |
|---|---|
| Lactose | 60 parts |
| Magnesium stearate | 5 parts |

The above components were intimately mixed, and the mixture was charged in capsules with 20 mg of the active agent contained in each.

EXAMPLE 3 (SUPPOSITORIES)

| Daunorubicin hydrochloride | 20 parts |
|---|---|
| Macrogol 4000 | 260 parts |
| Macrogol 1500 | 1240 parts |

The above components were intimately mixed, and the mixture was shaped into suppositories with 20 mg of the active agent contained in each piece.

What is claimed is:

1. A method of treating feline leukemia virus cells comprising administering thereto an effective amount of a compound selected from the group consisting of daunorubicin, doxorubicin and pharmaceutically acceptable salts thereof.

2. A method of inhibiting the production of retrovirus comprising administering thereto an effective amount of a compound selected from the group consisting of daunorubicin, doxorubicin and pharmaceutically acceptable salts thereof.

3. A method of inhibiting the production of retrovirus as set forth in claim 2, wherein said retrovirus is HTLV-1.